United States Patent [19]
Adelstein et al.

[11] Patent Number: 5,324,508
[45] Date of Patent: Jun. 28, 1994

[54] METHOD FOR DECREASING THE FORMATION OF SCAR TISSUE USING A PURIFIED MAMMALIAN MONOKINE PRODUCT

[75] Inventors: Edward H. Adelstein; Barbro A. L. Barrett; William H. Thornton, Jr., all of Colombia, Mo.

[73] Assignee: The Curators of the University of Missouri, Columbia, Mo.

[21] Appl. No.: 899,225

[22] Filed: Jun. 16, 1992

Related U.S. Application Data

[60] Continuation of Ser. No. 733,591, Jul. 22, 1991, abandoned, which is a division of Ser. No. 535,835, Jun. 11, 1990, abandoned.

[51] Int. Cl.$^5$ .............. A61K 45/05; C12P 21/06; C12N 5/00
[52] U.S. Cl. .................. 424/85.1; 435/69.5; 435/240.2; 435/240.23; 435/240.3
[58] Field of Search ............. 435/69.5, 70.1, 70.3, 435/240.2, 240.21, 240.23, 240.3, 240.31; 424/85.1, 520

[56] References Cited

U.S. PATENT DOCUMENTS 4,929,442 5/1990 Powell ................... 424/85.2

OTHER PUBLICATIONS

Korn et al., J. Clin. Invest., vol. 65, pp. 543–554 (Feb. 1980).
Fukasawa et al., J. of Surg. Research, vol. 45, pp. 460–466 (1988).
Concannon et al., Am. Burn Assoc. Annual Meeting, (Abstract).
Book by D. W. King, M.D. et al. entitled General Pathology: Principles and Dynamics, section entitled Inflammation and Repair: Multicellular Response to Injury, Lea and Feibinger (1983) Philadelphia, pp. 73–75 and 79–81.
Article by William Browder, M.D. et al. -Effect of Enhanced Macrophage Function on Early Wound Healing, Surgery, vol. 104, No. 2, 1988, pp. 224–229.
Joseph Giangiacomo, M.D. entitled Histopathology of Triamcinolone in the Subconjunctiva in Ophthalmology, vol. 94, No. 2, Feb. 1987, pp. 149–153.
Daniel A. Rappolee, et al. entitled Wound Microphages Express TGF- and other Growth Factors in Vivo: Analysis by mRNA Phenotyping, Science, vol. 241, Aug. 5, 1988, pp. 708–712.
Joseph Giangiacomo, M.D. et al. entitled The Effect of Preoperative Subconjunctival Triamcinolone Administration on Glaucoma Filtration in Arch. Ophthalmol, vol. 104, Jun., 1986, pp. 838–841.
C. W. Turck et al. entitled Immunological Mediators of Wound Healing and Fibrosis, Journal of Cellular Physiology-Supplement vol. 5, pp. 89–93, 1987.
Article by H. Orita et al. entitled Modulation of Fibroblast Proliferation and Transformation by Activated Microphages During Post Operative Peritoneal Reepithelialization–American Journal of Obstretics and Gynecology, vol. 155, pp. 905–911, Oct., 1986.

*Primary Examiner*—Douglas W. Robinson
*Assistant Examiner*—Susan M. Dadio
*Attorney, Agent, or Firm*—Gerstman, Ellis & McMillin, Ltd.

[57] ABSTRACT

Fibroblast growth in a healing wound, and the consequent formation of scar tissue, may be inhibited by application of a macrophage monokine product, the macrophage monokine having a molecular weight of no more than about 10,000 Dalton. The macrophage monokine appears to be generally effective across species of mammals, and also exhibits the characteristic of stimulating hair growth on skin cells to which it is applied.

11 Claims, No Drawings

METHOD FOR DECREASING THE FORMATION OF SCAR TISSUE USING A PURIFIED MAMMALIAN MONOKINE PRODUCT

This is a continuation of application Ser. No. 07/733,591, filed Jul. 22, 1991, now abandoned, which, in turn, is a division of application Ser. No. 535,835, filed Jun. 11, 1990 now abandoned.

BACKGROUND OF THE INVENTION

This present invention relates to a new therapeutic product which has been found to inhibit fibroblast growth in a healing wound or the like, which has the effect of suppressing scar formation in the healing wound, whether surgically or accidentally formed. Additionally, it has been found that the same therapeutic product has a tendency to stimulate hair growth when applied to skin cells, which may be of value with respect to the healing of scalp injuries, or it may be used for the stimulation of hair growth per se without the presence of an injury.

In the prior art, there are various techniques which have been used in attempts to minimize scarring during the healing of the wound, whether the wound is an accidental wound or a surgically created incision. Corticosteroids have been used topically and systemically as anti-inflammatory agents, and to prevent keloid formation. However, the use of corticosteroids to minimize scarring can have significant disadvantages. Itching, dryness, secondary infection and skin atrophy can occur. Also, systemic absorption is possible, leading to additional adverse effects such as impaired wound healing, fragile skin, bruising, ecchymoses and subcutaneous fat atrophy. Other adverse effects may result from particularly the systemic dosage of corticosteroids which are well known, including adverse affects on the gastrointestinal tract and the central nervous system.

Another technique for minimizing scarring is the use of surgical staples, but they are not practical for the use in cosmetic surgery requiring small incisions. Furthermore, the application of surgical staples, or the suturing that goes with plastic surgery, is a highly skilled procedure.

In accordance with this invention, a new anti-scarring therapeutic product has been discovered which, as stated, has the added characteristic of stimulating the growth of hair at least in some circumstances. The anti-scarring agent of this invention may be applied topically, or it may be administered in other desired ways such as by localized injection in the vicinity of a wound.

Without wishing to be limited to any one theoretical explanation for the action of the therapeutic product of this invention, it appears to suppress the multiplication of fibroblasts in a healing wound, with the consequential result that the formation of scar tissue in the healing wound is suppressed.

DESCRIPTION OF THE INVENTION

In accordance with this invention, one can inhibit fibroblast growth in a healing wound by the method which comprises: applying to living cells adjacent the wound an effective dose of a monokine produced by the culturing of macrophage cells, typically mammalian macrophage cells. Present indications show that at least the cells of rabbit and man can produce a monokine which is effective in their own species, but is also effective across species boundaries including horse, rabbit and man. By such an application of the monokine of this invention, the formation of scar tissue during the healing process may be inhibited, and in some cases, scar tissue can actually regress. Additionally, as mentioned above, hair growth may be stimulated by the application to in vivo skin cells of an effective does of the monokine produced by the culturing of macrophage cells.

While typically the healing wound in which fibroblast growth can be inhibited is at the skin surface of the body, and a purpose of this invention is to avoid unsightly scarring, it is contemplated that the invention of this application may also be applied to internal wounds of various kinds to avoid clinically undesirable outcomes which result from excessive fibroblast involvement in the healing. For example, it is contemplated that fibroblast involvement may be suppressed in accordance with this invention in a wide variety of diseases and conditions in which the clinical outcome can be improved by the suppression of fibroblasts, for example:

1. Pulmonary fibrosis associated with chronic obstructive lung disease.
2. Stricture formation in urological operations, orthopedic procedures in joint reconstruction, and esophageal strictures following surgery.
3. Reconstructive facial surgery.
4. Burn reconstruction and treatment
5. Abdominal adhesions following surgery.
6. Trabeculectomy fibrosis in glaucoma filtration.

The monokine of this invention is preferably purified to be substantially cell free for use in the therapeutic process, and is preferably substantially free of macrophage monokine products having a molecular weight of above about 10,000 Dalton. This may be accomplished in conventional manner by means of dialysis, centrifugation, or the like. A number of higher molecular monokines stimulate fibroblast activity and are thus desirably removed. The term "monokine" implies a product secreted by a cell of monocytic origin, called herein a mononuclear cell.

The macrophage monokine product which is the active ingredient in accordance with this invention may be more than one species of product having molecular weights of typically no more than about 10,000 Dalton, and preferably on the order of 4,000 to 6,000 Dalton or less, which is of significantly lower molecular weight than most other known macrophage monokines. At least one species of the macrophage monokine used in this invention exhibits resistance to deactivation by trypsin and carboxypeptidase A.

The purified macrophage monokine product may be mixed in a pharmaceutically effective concentration with any appropriate pharmaceutically acceptable carrier. For example, the active monokine product of this invention may be formulated as a lotion or ointment. Otherwise, it may be formulated as an injectable material in any pharmaceutically acceptable, typically osmotically balanced injection solution such as 0.9 percent saline.

Accordingly, the macrophage monokine of this invention may be topically applied as ointment or oil base material onto a wound (traumatic or burn) which is either accidentally created or formed through surgery, to suppress scarring action. Additionally, in deeper wounds, the monokine in a pharmaceutically effective injectable preparation may be injected or otherwise released into the area of the tissue surrounding the wounds so as to suppress the scarring reaction.

Also, an ointment or lotion of the macrophage monokine may be applied to the skin to stimulate hair growth.

The purified macrophage monokine of this invention may be produced by culturing macrophage cells in a cell culture media to cause the cells to excrete monokine into the media. One then separates the cells from the culture media, and removes components from the culture media having a molecular weight typically above about 10,000 Dalton, to obtain a solution of a purified monokine.

The macrophage cells are mammalian cells, for example rabbit or human, which may be obtained by peritoneal lavage in a generally conventional manner.

The components preferably above at least about 5,000 to 6,000 Dalton may be removed by dialysis, a centrifugation technique, or any other desired means. During the culturing step, the macrophage cells are preferably allowed to adhere to a surface in contact with the culture media. Typically, the cells adhere to the bottom of plastic flasks used as culture containers. Without wishing to be limited to any specific theory of operation, it is possible that the monokine of this invention is released by the macrophage cells as a consequence of the cells' adhesion to the container walls. At any rate, most of the relatively low molecular weight monokine used in this invention is produced during the first 72 hours of macrophage incubation, so that it is generally not preferred to continue the incubation beyond about 72 hours without separating the macrophage cells from the culture media and harvesting the purified monokine. After being removed from the culture media, the cells can be treated with trypsin to cause their release from the surface to which they adhere (such as the plastic flask wall). The resulting cell suspension may then be divided by dividing the solution in which they reside, centrifuged and washed to remove the trypsin, and then placed in media flasks with new cell culture media. After such treatment, the cultured, macrophage cells frequently produce more of the monokine used in this invention within about a 72 hour period.

DESCRIPTION OF SPECIFIC EMBODIMENTS

Example 1

A. New Zealand white albino rabbits were anesthetized with Promazine HCl 1M, followed after 5 minutes by Ketamine HCl. A fourteen gauge catheter (ANGIOCATH) was inserted after forming a surgical incision into the peritoneal cavity, and 50/ml. of pure mineral oil (USP light) was injected. The catheter was then removed.

After six days, the rabbits were catheterized in similar manner, with the peritoneal catheter being once again inserted, and 200 ml. of 0.9% sodium chloride solution run through the catheter to fill the peritoneal cavity, followed by draining of the peritoneal cavity and collection of the resulting peritoneal drainage solution.

A two-phase mixture of mineral oil and peritoneal dialysate was collected. The aqueous phase was aliquoted into 15/ml. conical centrifuge tubes and centrifuged at 150 G for ten minutes. The supernatant was discarded and the resulting cell pellets from centrifugation were resuspended in 150 ml. of tissue culture media comprising serum free McCoy's media with 4 micrograms per ml of Gentamicin and 0.2% lactalbumin enzymatic hydrolysate. The cells were then centrifuged once again, washed once with the above described media, and placed into tissue culture flasks in such media, following which the cells settle and adhere to the bottoms of the tissue culture flasks.

The cells were incubated for forty minutes at a thirty-seven degree C., seven percent carbon dioxide, humidified atmosphere. Monocytes adhere in this incubation period to the bottom of the flasks, following which the media containing nonadherent cells was removed. The monocytes were gently rinsed twice with the above-described media without lactalbumin, which was removed, and fresh media was returned to the flask. The monocytes were then incubated for 72 hours at 37 degrees C., in a humidified atmosphere containing seven percent carbon dioxide.

After this treatment, the media was once again removed from the flasks, and found to contain the macrophage monokine of this invention, having a molecular weight of about 3,000 to 4,000 Dalton. The media may be centrifuged to remove any cells.

The media from the flasks may also be centrifuged to remove materials having a molecular weight above about 4,000 Dalton, following which the supernatant, containing the purified macrophage monokine product of this invention, may be removed. The centrifugation may take place through known molecular weight filters. The resulting supernatant may be filtered through a 0.22 micron filter for sterility, and may be then ready for addition in pharmaceutically effective concentration to a pharmaceutically acceptable carrier such as an ointment base or a substantially isotonic injectable solution, after concentration by vacuum removal of water if desired.

Following this, New Zealand white rabbits received 10 cm longitudinal dorsal incisions. Two ml. of the above-produced monokine solution (or alternatively a control media) was then injected intradermally daily about each incision for 7 or 14 days postoperatively.

The dorsal incisions were made under general anesthesia and closed with surgical staples. Following the daily application of the monokine media or control media, the animals were sacrificed, and the scars with surrounding tissue were removed for histologic examination with staining of the sections with Hematoxylin and Eosin. In the incisions which were treated with the monokine, a significant decrease in the fibroblast number was noted versus the corresponding incisions treated with the control. After 7 days of injections, the number of fibroblasts noted adjacent the incisions were reduced by 33 percent in the group treated with the monokine of this invention, when compared with the control group. After 14 days of injections, there was a 27 percent decrease in fibroblast proliferation when compared with the control group.

It was noted that hair growth was stimulated by the monokine treatment adjacent the incisions.

B. Rabbit ocular fibroblasts were grown in cell culture in the same media used for macrophage culture described above. Established fibroblast were removed from culture flasks and diluted in the same media to a concentration of 1.5 to $2 \times 10^5$ cells per ml. Aliquots of 100 microliters of the diluted cells were added to cell culture microliter plates, followed by 100 microliters of the monokine media prepared as above, or alternatively, monokine-free media as a control.

The cells were incubated for 24 hours, followed by the addition of 0.4 microcuries of 3H-thymidine in 50 microliters of media, followed by an additional 24 hour incubation. At the end of this incubation, the cells were harvested using a MASH II harvester and counted in a beta-scintillation counter. The results were expressed in a percent inhibition, representing the decrease in counts per minute of the monokine-treated cells, when compared with the control, untreated cells.

When monokine which had been separated from higher molecular weight monokines by centrifugation was used, the minimum inhibition in any experiment was 22 percent, while the maximum inhibition was 86 percent. The majority of the experimental results for nondialyzed monokine ranged between about 55 and 75 percent.

The results for monokine which had been separated by dialysis provided a percent inhibition ranging from 25 to 62 percent.

The above results came from 26 different assays.

C. In one experiment, human ocular fibroblasts were treated and tested in the manner of section B above. In this case the inhibition of cell growth caused by the monokine of this invention separated by centrifugation was 93-94 percent.

D. In a single experiment, human scar fibroblasts were tested in the manner of section B above. In this instance, the cell-growth inhibition caused by the monokine (separated by centrifugation) above was 89-92 percent.

E. A suspension of human ocular fibroblasts ($2 \times 10^5$ cells/cc.) were placed into a culture system. After one hour of incubation at 37° C. in a 7% $CO_2$ atmosphere, the liquid media is discarded, with the fibroblasts adhering to the culture dish. A one percent agar media is applied to the dish and allowed to solidify. Holes were then punched in the solidified agar, and filled with the monokine solution prepared above or, alternatively, a control media. After twenty-four hours of incubation the culture was examined and photographed under inverted phase microscopy. Clear evidence was seen of significant inhibition of growth of fibroblast cells within and around each of the holes, while dense fibroblast growth was noted in peripheral areas spaced from the holes.

The utilization of a serum-free media as in this example eliminates many factors which would interfere with the isolation of the monokine used in this invention. Additionally, by this means one can rule out the need for serum supplementation in the crude monokine product to obtain inhibitory activity.

EXAMPLE 2

The macrophage monokine product produced in the previous example, used as a complete supernatant, with monokines over about 4,000 Dalton removed, was formulated into a conventional cream base formulation to provide a concentration of 1 ml. of complete supernatant per 10 g. of cream base. In two separate cases, horses which were afflicted with granulomas on the legs were treated by daily application of the monokine-containing cream base to the granuloma. A granuloma is created in a horse from a skin injury, which causes a proliferation of scar tissue, resulting in a prominent, ugly, raised scar. Both of the horses had unsuccessfully received conventional veterinary treatments for the granulomas that were forming from injuries, one for over a year.

After several weeks of treatment with the monokine cream, in both cases the granuloma receded, and a more normal healing of the skin injury took place.

It was noted that the monokine cream stimulated hair growth in the area of treatment.

The above has been offered for illustrative purposes only, and is not intended to limit the scope of the invention of this application, which is as defined in the claims below.

That which is claimed is:

1. A method of decreasing the formation of scar tissue during the healing of an injury comprising applying a purified mammalian monokine product to the site of an injury in an effective dose to decrease the formation of scar tissue during the healing of said injury, said purified monokine being produced by the steps of:

culturing mammalian macrophage cells in a cell culture media for a period of no more than about 72 hours while allowing the cells to adhere to a surface, to cause said cells to excrete monokine into said media; and separating said cells from said culture media; and removing from said culture media monokine components having a molecular weight above about 6,000 Dalton to obtain a solution of said purified monokine which is essentially free of said components having a molecular weight of above about 6,000 Dalton.

2. The method of claim 1 in which said solution of purified monokine is essentially cell-free.

3. The method of claim 1 in which said monokine is produced by the culturing of human macrophage cells.

4. The method of claim 1 in which said monokine is purified by separating out impurities having molecular weights of above about 4,000 Dalton.

5. The method of claim 1 in which said macrophage cells are obtained by peritoneal lavage.

6. The method of claim 1 in which said cell culture media is serum free.

7. The method of claim 1 in which the purified monokine product is applied to a granuloma of a horse.

8. The method of claim 1 in which said monokine is produced by the culturing of human macrophage cells and is purified by separating out monokine impurities having molecular weights of above about 4,000 Dalton.

9. The method of claim 8 in which said solution of purified monokine is essentially cell-free.

10. The method of claim 9 in which said macrophage cells are obtained by peritoneal lavage.

11. The method of claim 10 in which said cell culture media is serum free.

* * * * *